United States Patent [19]
Kitaevich et al.

[11] Patent Number: 5,344,568
[45] Date of Patent: * Sep. 6, 1994

[54] HEMOFILTRATION SYSTEM AND METHOD

[75] Inventors: Yuli Kitaevich, Milford; Nat Hemasilpin, Fairfield; J. Gabriel Marchevsky, Cincinnati; John J. Bissler, Cincinnati; George Benzing, III, Cincinnati; Paul T. McEnery, Cincinnati, all of Ohio

[73] Assignee: Children's Hospital Medical Center, Cincinnati, Ohio

[ * ] Notice: The portion of the term of this patent subsequent to May 18, 2010 has been disclaimed.

[21] Appl. No.: 62,928

[22] Filed: May 17, 1993

Related U.S. Application Data

[63] Continuation of Ser. No. 775,183, Oct. 11, 1991, Pat. No. 5,211,849.

[51] Int. Cl.$^5$ ............................................. B01D 61/100
[52] U.S. Cl. ..................................... 210/645; 210/85; 210/90; 210/96.1; 210/97; 210/134; 210/138; 210/143; 210/195.2; 210/257.1; 210/258; 210/321.71; 210/416.1; 210/433.1; 210/646; 210/739; 210/805; 210/929; 604/4; 604/5; 604/6
[58] Field of Search ............... 210/85, 90, 96.1, 97, 210/101, 134, 138, 143, 195.2, 257.1, 257.2, 258, 259, 321.71, 416.1, 433.1, 645, 646, 805, 739, 649, 929; 604/4, 5, 6; 422/48; 177/45, 50

[56] References Cited

U.S. PATENT DOCUMENTS

| | | | |
|---|---|---|---|
| 4,844,810 | 7/1989 | Richalley et al. | 210/646 |
| 5,200,090 | 4/1993 | Ford et al. | 210/739 |
| 5,211,849 | 5/1993 | Kitaevich et al. | 210/645 |

FOREIGN PATENT DOCUMENTS 2397197 2/1979 France.

OTHER PUBLICATIONS

Sartorius/Hemoprocessor 40020 Operating Instructioons, Sep. 1984.
Gambro/Hemofiltration AK-10 System/Operator's Manual for Hemofiltration BMM 10-1, HFM 10-1, May 1986.
Hospal Instruction Manual BSM 22SC, Rev. A, pp. 29, 30 & 57, Mar. 1990.
COBE Centry System 3 Dialysis Control Unit Operator's Manual, pp. 1-21, 1-22, 3-29, 5-1, 5-2 & 7-9, Sep. 1988.
Sartorius Hemofilter, date unknown.
Sartorius Membranfilter Hemofilter and Hemoprocessor, A New System for Hemofiltration, date unknown.

*Primary Examiner*—Robert A. Dawson
*Assistant Examiner*—Sun Uk Kim
*Attorney, Agent, or Firm*—Wood, Herron & Evans

[57] ABSTRACT

A multipurpose hemofiltration system and method are disclosed for the removal of fluid and/or soluble waste from the blood of a patient. The system and method are equally applicable to adult, pediatric and neonatal patients. The system continuously monitors the weight of infusate in a first reservoir and drained fluid in a second reservoir and compares those weights to corresponding predetermined computed weights. When necessary, the pumping rates of the infusate, drained fluid and blood are adjusted in order to achieve a preselected amount of fluid removal from the patient's blood in a preselected time period. Application of this system and method provide repeatable and highly precise results.

11 Claims, 1 Drawing Sheet

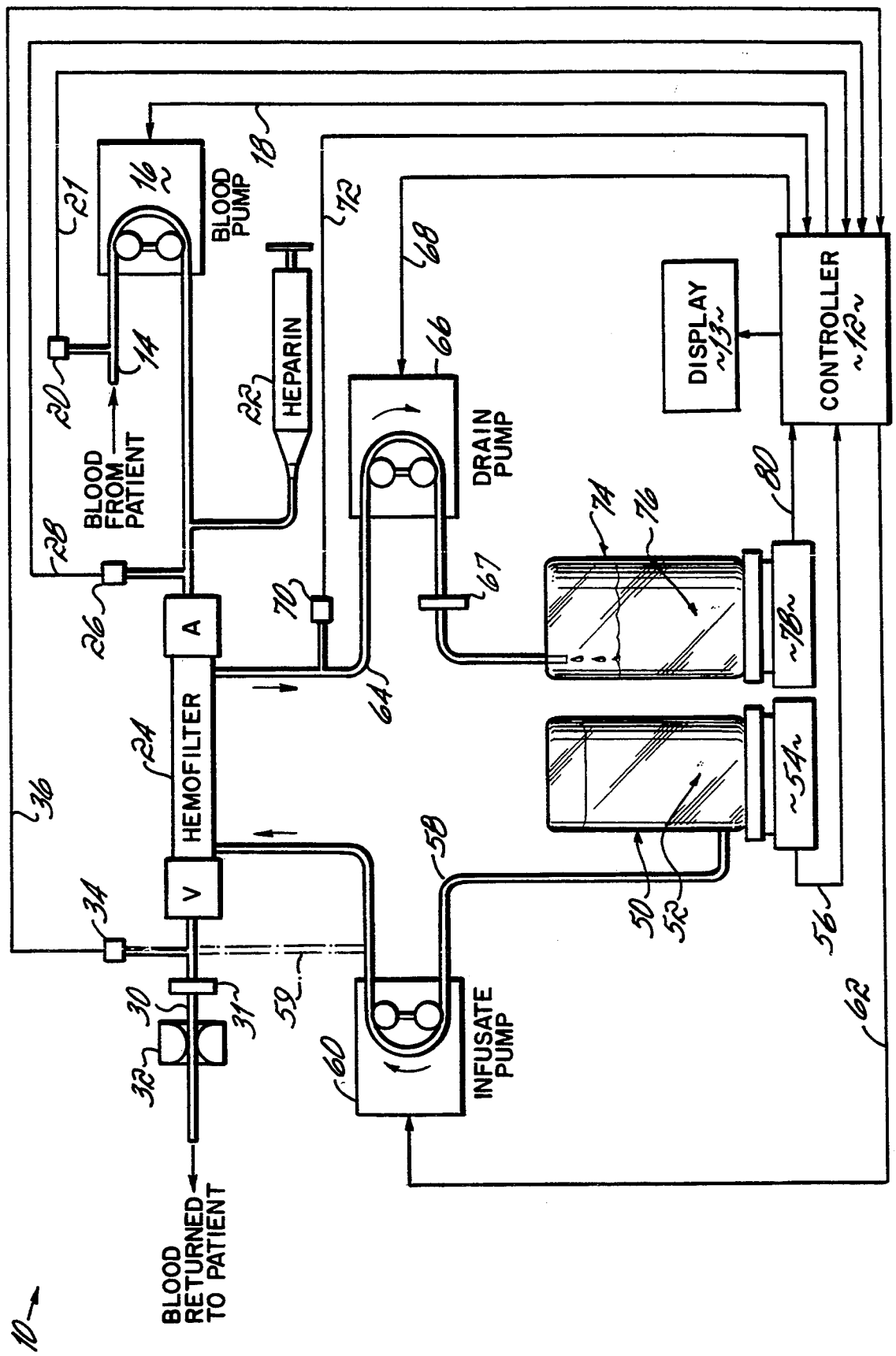

HEMOFILTRATION SYSTEM AND METHOD

This is a continuation of application Ser. No. 07/775,183, filed Oct. 11, 1991, now U.S. Pat. No. 5,211,849, issued May 18, 1993.

FIELD OF THE INVENTION

The present invention is directed to a system and method of blood filtration, and particularly a continuous system and method for the regulation of the rate of filtration of fluid and/or soluble waste from the blood of a patient.

BACKGROUND OF THE INVENTION

For various reasons, including illness, injury or surgery, patients may require replacement or supplementation of their natural renal function in order to remove excess fluid or fluids containing dissolve waste products from their blood. Several procedures known for this purpose are dialysis, hemodialysis, hemofiltration, hemodiafiltration and ultrafiltration; another related procedure is plasmapheresis. The specific procedure employed depends upon the needs of the particular patient. For example, dialysis is used to remove soluble waste and solvent from blood; hemofiltration is used to remove plasma water from blood; hemodiafiltration is used to remove both unwanted solute (soluble waste) and plasma water from blood; ultrafiltration is a species of hemofiltration; and plasmapheresis is used to remove blood plasma by means of a plasmapheresis filter. Because the replacement of renal function may affect nutrition, erythropoiesis, calcium-phosphorus balance and solvent and solute clearance from the patient, it is imperative that there be accurate control of the procedure utilized. The accurate control of the rate of removal of intravascular fluid volume is also important to maintain proper fluid balance in the patient and prevent hypotension.

Various systems have been proposed to monitor and control renal replacement procedures. For example, U.S. Pat. No. 4,132,644 discloses a dialysis system in which the weight of dialyzing liquid in a closed liquid container is indicated by a scale. After the dialyzing liquid flows through the dialyzer, the spent liquid is returned to the same container and the weight is again indicated. Since the container receives the original dialyzing liquid plus ultra-filtrate, the amount of ultrafiltrate removed from the patient is equal to the increase in total weight in the container. This system is not driven by a weight measuring device and does not offer precise control of the amount of liquids used in the procedure.

U.S. Pat. No. 4,204,957 discloses an artificial kidney system which utilizes weight measurement to control the supply of substituate fluid to a patient. In this system, the patient's blood is pumped through a filter and the filtrate from the blood is discharged to a measuring vessel associated with a weighing device. A second measuring vessel containing substituate fluid is associated with a second weighing device and is connected to the purified blood line. By means of a pump, the substituate fluid and the purified blood are pumped back to the patient. The first and second weighing devices are coupled to one another by a measuring system in such a way that a fixed proportion of substituate is supplied to the purified blood stream from the second measuring vessel depending on the weight of the filtrate received in the first measuring vessel. This system does not utilize circulating dialysate fluid in the blood filtration.

U.S. Pat. No. 4,767,399 discloses a system for performing continuous arteriovenous hemofiltration (CAVH). The disclosed system relies upon utilizing a volumetric pump to withdraw a desired amount of fluid from the patient's blood and return a selected amount of fluid volume to the patient.

U.S. Pat. No. 4,923,598 discloses an apparatus for hemodialysis and hemofiltration which comprises an extracorporeal blood circuit including a dialyzer and/or filter arrangement. The system determines fluid withdrawal per unit time and total amount of fluid withdrawn by utilizing flow sensors in conjunction with an evaluating unit located upstream and downstream of the dialyzer or filter arrangement in the blood circuit.

U.S. Pat. No. 4,728,433 discloses a system for regulating ultrafiltration by differential weighing. The system includes a differential weighing receptacle having an inlet chamber and an outlet chamber which allows a fixed amount of fresh dialysate, by weight, to flow through the hemodialyzer. This system operates in a sequence of weighing cycles during which the amount of ultrafiltrate removed from the blood may be calculated. Additionally, the ultrafiltration rate for each weighing cycle may be calculated. This system provides a mechanism for determining and regulating the amount of ultrafiltrate removed from the blood while delivering dialysate to the patient in alternating fill and drain cycles of the inlet and outlet chambers of the differential weighing receptacle.

The need exists for a multipurpose renal function replacement/supplementation system which is accurate, reliable, capable of continuous, long-term operation, and which can be used effectively on adult, pediatric and neonatal patients.

SUMMARY OF THE INVENTION

The present invention is directed to a multipurpose system and method for removal of fluid and/or soluble waste from the blood of a patient: ultrafiltration only, hemodiafiltration, hemodiafiltration and ultrafiltration, and plasmapheresis with or without fluid replacement. The system and method of the present invention can provide reliable, longterm operation (5-10 days) with a great degree of accuracy (on the order of ±2 grams regardless of the total volume of fluid passing through the system). The system and method of the invention are advantageous because of the multipurpose nature thereof, the repeatability and accuracy of the processes, and the simultaneous, continuous flow of fluids in an extracorporeal blood circuit, while being equally applicable to adult, pediatric and neonatal patients.

As used herein the term "hemofiltration" is to be broadly construed to include hemodialysis, hemofiltration, hemodiafiltration, ultrafiltration and plasmapheresis processes. As used herein, the term "infusate" is defined to include dialysate fluid or any other fluids which may be supplied to the patient as a part of the hemofiltration procedures.

In a preferred embodiment, the system of the present invention includes a hemofilter, a blood pump for pumping blood from a patient through the hemofilter and back to the patient, and suitable tubing for carrying the pumped blood to and from the patent. The system further includes a first reservoir for maintaining a supply of infusate, a first weighing means for continuously monitoring the weight of the infusate and generating signals correlated to the monitored weight, and a first pump for pumping the infusate from the first reservoir to the hemofilter or appropriate blood tubing access port. A second reservoir receives drained fluid (e.g., spent infusate or ultrafiltrate, including the fluids and solutes removed from the blood) from the hemofilter, and a second weighing means monitors the weight of the drained fluid and generates signals correlated to the monitored weight. A second pump pumps the drained fluid from the hemofilter to the second reservoir. The system also includes a controller operably connected to the blood pump, the infusate pump, the drain pump and the first and second weighing means.

The controller periodically interrogates, at predetermined intervals, the signals that are continuously generated by the first and second weighing means and is designed to determine therefrom the weight of infusate and drained fluid in the first and second reservoirs at the predetermined intervals. The rate of fluid withdrawal from the blood is also determined. The controller compares the infusate and drained fluid weights to corresponding predetermined computed weights in the memory of the controller, and, when necessary, the controller generates signals which adjust the pumping rates of the infusate and drained fluid pumps in order to achieve a preselected amount of fluid removal from the patient's blood. Additionally, the controller is programmed to operate the infusate and drained fluid pumps only when the blood pump is operating. Furthermore, the blood pump is operably connected to and is responsive to signals generated by the controller to vary the flow rate of the blood through the hemofilter as required to achieve the desired level of fluid removal from the blood.

In a preferred embodiment of the method of the present invention, blood from a patient is pumped through a hemofilter and a supply of infusate, which is maintained in a first reservoir, is pumped from the first reservoir through the hemofilter, countercurrent to the blood. The weight of infusate in the first reservoir is continuously monitored and signals correlated to that weight are generated. Drained fluid (e.g., spent infusate) is pumped from the hemofilter and is received in a second reservoir. The weight of the drained fluid in the second reservoir is continuously monitored and signals correlated thereto are generated. The signals correlated to the weight of infusate and drained fluid are interrogated at regular intervals (for example every minute) by a system controller and are compared to corresponding predetermined computed weights in the memory of the controller. The controller determines the amount and rate of fluid withdrawal from the patient's blood. If those values differ from preselected, pre-programmed desired values, the controller generates signals which independently adjust the pumping rates of the infusate and drained fluid pumps so as to achieve the desired amount of fluid removal.

The advantages of the system and method of the present invention are achieved at least in part due to the continuous monitoring and periodic interrogation of the fluid weights and the adjustment of fluid pumping rates, including the blood pumping rate, so as to achieve ideal or nearly ideal fluid removal and replacement if necessary from a patient's blood. Further features and advantages of the system and apparatus of the present invention will become apparent with reference to the FIGURE and the detailed description which follows.

BRIEF DESCRIPTION OF THE FIGURE

The FIGURE is a diagrammatic representation of one embodiment of the system of the present invention; an alternative embodiment is shown in phantom.

DETAILED DESCRIPTION OF THE INVENTION

The FIGURE shows a diagrammatic representation of a preferred embodiment of the system of the present invention. The portion of the FIGURE shown in phantom represents an alternative embodiment of the present invention which will be described hereinbelow. Hemofiltration system 10 is operated and controlled by a suitable controller designated generally as 12. Controller 12 may be a programmable computer such as be COMPAQ 386/S having a display 13 and is operably connected to various components of hemofiltration system 10, as will be described in greater detail hereinafter.

In operation, blood is pumped from a patient (not shown), which may be an adult, pediatric or neonatal patient, through a suitable catheter (not shown) and input tubing 14 by means of a blood pump 16. Blood pump 16, which is preferably of the roller type, is operably connected to controller 12 by line 18. One suitable blood pump is the RS-7800 Minipump manufactured by Renal Systems, Minneapolis, Minn. Input tubing 14 through which the patient's blood is pumped preferably includes a pressure transducer 20 upstream of pump 16. Pressure transducer 20 is operably connected to controller 12 via line 21. Means are included downstream of blood pump 16 for accessing input tubing 14 to enable the injection or infusion of desired fluids, including medications and anti-clotting compounds such as heparin, into the patient's blood. The injection or infusion of such fluids to the blood may be accomplished in any suitable manner; the FIGURE shows diagrammatically a syringe and tube arrangement 22, but it will be appreciated that other means could be employed for the same purpose.

The patient's blood is pumped through hemofilter 24 by blood pump 16. Filters of the type suitable for use in the system of the present invention are readily available; one example of a suitable hemofilter is the Diafilter manufactured by AMICON, Danvers, Mass. Where the present system is used to perform plasmapheresis, a suitable plasmapheresis filter such as the Plasmaflo manufactured by Parker Hannifin, Irvine, Calif. can be employed.

Input tubing 14 includes a second pressure transducer 26 slightly upstream of hemofilter 24. Pressure transducer 26 is operably connected to controller 12 via line 28. The patient's blood exits hemofilter 24, passes through output tubing 30 and is returned to the patient via any suitable means such as a venous catheter arrangement (not shown). Output tubing 30 preferably includes a suitable blood flow detector 31 which verifies that there is blood flow in the system and an air bubble/foam control device such as air bubble clamp 32 to prevent the passage of air bubbles to the patient. Blood flow detector 31 and air bubble clamp 32 may be operably connected (not shown) to controller 12 or directly to the pumps to interlock all pumps upon detection of any air bubbles in the blood or upon the cessation of blood flow. A suitable foam-bubble detector is the RS-3220A manufactured by Renal Systems. Output tubing 30 also preferably includes a pressure transducer 34 immediately downstream of hemofilter 24. Pressure transducer 34 is operably connected to controller 12 via line 36.

A first reservoir 50 maintains a supply of suitable dialysate or other fluid, referred to herein generally as infusate 52. The infusate-containing reservoir 50 is supported by a weighing device such as electronic scale 54 which is operably connected to controller 12 via line 56. Infusate 52 is pumped from reservoir 50 via tubing 58 by means of infusate pump 60, which is preferably of the roller variety. A suitable pump for this purpose is a 3½ Roller Pump manufactured by PEMCO, Cleveland, Ohio. Infusate pump 60 is operably connected to controller 12 via line 62 and pumps infusate 52 through hemofilter 24 countercurrent to the blood pumped therethrough. In accordance with known principles, infusate 52 may extract certain components (fluids and/or soluble waste) from the blood passing through hemofilter 24. The fluid drained from hemofilter 24 includes spent infusate and the components removed from the blood, which are referred to herein as drained fluid 76. In an alternative embodiment wherein system 10 is used as a fluid or plasma replacement system, e.g., to perform plasmapheresis, the infusate (which may be blood plasma) from reservoir 50 is pumped via tubing 59 (shown in phantom) to blood output tubing 30, thereby replacing the fluid volume removed from the blood. In this embodiment, the drained fluid 76 from hemofilter or plasmapheresis filter 24 does not include any spent infusate since the infusate is pumped directly to blood output tubing 30 and supplied to the patient.

The drained fluid 76 is pumped from hemofilter 24 through outlet tubing 64 by means of drain pump 66, which is preferably a roller-type pump, and may be the same as infusate pump 60. Drain pump 66 is operably connected to controller 12 via line 68. Output tubing 64 preferably includes a pressure transducer 70 downstream of hemofilter 24, but upstream of drain pump 66. Pressure transducer 70 is operably connected to controller 12 via line 72. Output tubing 64 also preferably includes a blood leak detector 67 which detects the presence of blood in the drained fluid 76, as may occur if hemofilter 24 ruptures. A suitable blood leak detector is sold by COBE, Lakewood, Colo. as model 500247000. Blood leak detector 67 may be operably connected (not shown) to controller 12 or directly to the pumps to interlock all pumps upon the detection of blood in the drained fluid. Drained fluid 76 pumped from hemofilter 24 is pumped into a second reservoir 74 which collects the drained fluid. Second reservoir 74 is supported by a weighing device such as electronic scale 78, which is operably connected to controller 12 via line 80.

Scales 54 and 78, may be model 140 CP sold by SETRA of Acton, Mass. continuously generate signals correlated to the weight of infusate and drained fluid contained in reservoirs 50 and 74, respectively. Those signals are continuously fed to controller 12, to which the scales are linked through an RS-232 interface. Likewise, pressure transducers 20, 26, 34 and 70 all continuously measure the pressure at their respective locations in hemofiltration system 10 and generate signals correlated thereto which are fed to controller 12. A suitable type of pressure transducer is model number 042-904-10 sold by COBE of Lakewood, Colo.

Controller 12 is preferably a programmable computer that is capable of sending and receiving signals from auxiliary equipment including pressure transducers 20, 26, 34 and 70, first and second scales 54 and 78, respectively, and blood pump 16, infusate pump 60, and drain pump 66. In operation, controller 12 interrogates, at regular intervals, the signals generated by first and second scales 54 and 78. From the signals, controller 12 determines the weight of infusate and drained fluid in the first and second reservoirs 50 and 74 at that point in time, and compares those weights to corresponding predetermined computed weights which have been programmed into and are stored by controller 12. By monitoring the weight of infusate in reservoir 50 and the weight of drained fluid in reservoir 74 at regular intervals, the rate of change of those weights and the rate of hemofiltration can be calculated by the computer portion of controller 12. When the weights deviate from the predetermined computed weights and/or the rate of hemofiltration deviates from a preselected, preprogrammed desired rate, controller 12 generates signals which control or adjust the rates at which blood pump 16, infusate pump 60 and drain pump 66 are operated, as necessary, to adjust the hemofiltration rate to the desired rate, or to stop the pumps when preselected limits have been reached. This is accomplished in a continuous manner; i.e., continuous signal generation, periodic interrogation of those signals and computation of the required weight and/or rate information, comparison to predetermined computed values and adjustment of the pumping rate of the pumps, as necessary, to achieve the desired amount and/or rate of hemofiltration.

Controller 12 is programmed so that infusate pump 60 and drain pump 66 are operated only when blood pump 16 is being operated. In the case when ultrafiltration is being performed, the pumping rate of drain pump 66 must equal the pumping rate of infusate pump 60 plus the desired ultrafiltration rate.

Controller 12 continuously receives signals from pressure transducers 20, 26, 34 and 70 and is programmed to generate alarm signals when high and low pressure limits are exceeded at any of the monitored locations. Furthermore, an alarm signal is generated when the pressure differential across hemofilter 24 exceeds a predetermined upper limit, as monitored specifically by pressure transducers 26, 34 and 70. Additionally, controller 12 may stop the pumps when preselected pressure limits (high or low) are exceeded, as for example may occur if the system tubing becomes occluded or ruptures or if pump occlusion occurs. Finally, controller 12 may signal when the infusate level in reservoir 50 reaches a predetermined lower limit and when the drained fluid level in reservoir 76 reaches a predetermined upper limit. Hemofiltration system 10 may also include suitable blood warmer and infusate warmer devices (not shown) to adjust and/or maintain the blood and infusate temperatures at desired levels. Such devices may also generate alarm signals when the fluid temperatures are outside of preselected limits.

Display 13 offers updated display of measured and computed parameters such as pressures, pressure differentials, temperatures, flow rates and amounts of infusate, drain and ultrafiltration, and alarm conditions. Controller 12 generates both visual and audible alarms and all the pumps are interlocked to prevent operation thereof under alarm conditions. Users have the option of disabling or unabling the alarms (the audible part of the alarm and its interlock with the pumps) to perform a procedure under close supervision. A printer (not shown) is operably connected (not shown) to controller 12 to generate a hard copy of procedural data currently displayed or stored at regular intervals, at the completion of a procedure or at any desired time.

Hemofiltration system 10 can be operated in one of two modes: 1) a manual mode wherein the pumping rates of blood pump 16, infusate pump 60 and drain pump 66 are provided by controller 12 when fixed voltages are applied; and 2) an automatic mode wherein the pumps are controlled by controller 12 when the desired hemofiltration amount or rate has been programmed into the controller. The automatic mode allows the system to be paused and later continued without losing previously measured and computed data.

It will be appreciated by persons skilled in the art that various modifications can be made to the system of the present invention without departing from the scope thereof which is defined by the appended claims.

What is claimed is:

1. Continuous hemofiltration system for removal of fluid from the blood of a patient, comprising:
   hemofiltration means;
   means for pumping blood from a patient through said hemofiltration means and back to the patient;
   a first reservoir for maintaining a supply of infusate;
   first pumping means for pumping the infusate from said first reservoir to said hemofiltration means;
   a second reservoir for receiving drained fluid from said hemofiltration means;
   second pumping means for pumping the drained fluid from said hemofiltration means to said second reservoir;
   weighing means for monitoring the weight of the infusate and the drained fluid and generating signals correlated thereto;
   control means operably connected to said blood pumping means and to each of said first and second pumping means and said weighing means, said control means comprising a computer programmed to operate said first and second pumping means only when said blood pumping means is operating;
   said blood pumping means being automatically responsive to signals generated by said control means to vary the flow rate of the blood through said hemofiltration means; and
   said control means being responsive to said signals generated by said weighing means and determining the weight of infusate and drained fluid in said first and second reservoirs, respectively, at regular intervals, comparing those weights to corresponding predetermined computed weights and adjusting the rates of pumping the infusate, drained fluid and blood so as to remove a preselected amount of fluid from the blood over a preselected time period.

2. The hemofiltration system of claim 1 wherein said hemofiltration means includes a hemofilter, input tubing through which blood is pumped to said hemofilter, output tubing through which blood is pumped from said hemofilter, feed tubing connecting said first pumping means to said hemofilter, and drain tubing connecting said second pumping means to said hemofilter.

3. The hemofiltration system of claim 2 further comprising:
   first pressure monitoring means for monitoring the pressure in said input tubing to said hemofilter;
   second pressure monitoring means for monitoring the pressure in said output tubing;
   third pressure monitoring means for monitoring the pressure in said drain tubing; and
   fourth pressure monitoring means for monitoring the pressure in said input tubing to said blood pump.

4. The hemofiltration system of claim 1 further comprising means for adding an anti-clotting medication to the blood prior to pumping the blood through said hemofiltration means.

5. Continuous hemofiltration system for removal of fluid from the blood of a patient, comprising:
   hemofiltration means;
   means for pumping blood from a patient through said hemofiltration means and back to the patient;
   a first reservoir for maintaining a supply of infusate;
   first pumping means for pumping the infusate from said first reservoir to the patient;
   a second reservoir for receiving drained fluid from said hemofiltration means;
   second pumping means for pumping the drained fluid from said hemofiltration means to said second reservoir;
   weighing means for monitoring the weight of the infusate and the drained fluid and generating signals correlated thereto;
   control means operably connected to said blood pumping means and to each of said first and second pumping means and said weighing means, said control means comprising a computer programmed to operate said first and second pumping means only when said blood pumping means is operating;
   said blood pumping means being automatically responsive to signals generated by said control means to vary the flow rate of the blood through said hemofiltration means; and
   said control means being responsive to said signals generated by said weighing means and determining the weight of infusate and drained fluid in said first and second reservoirs, respectively, at regular intervals, comparing those weights to corresponding predetermined computed weights and adjusting the rates of pumping the infusate, drained fluid and blood so as to remove a preselected amount of fluid from the blood over a preselected time period.

6. Hemofiltration method for removal of fluid from the blood of a patient, comprising:
   pumping blood from a patient through hemofiltration means and back to the patient;
   maintaining a supply of infusate in a first reservoir;
   pumping the infusate to the hemofiltration means;
   monitoring the weight of the infusate and generating signals correlated thereto;
   pumping drained fluid from the hemofiltration means into a second reservoir;
   monitoring the weight of the drained fluid and generating signals correlated thereto;
   controlling the pumping of the blood, infusate and drained fluid by means of a computer programmed to operate the pumps for infusate and drained fluid only when the blood is being pumped, said computer being responsive to the infusate and drained fluid weight signals;
   said blood pumping operation being automatically responsive to signals generated by said computer to vary the flow rate of the blood through the hemofiltration means; and
   determining, at regular intervals, the weight of infusate in the first reservoir and the weight of drained fluid in the second reservoir, comparing those weights to corresponding predetermined ideal weights and adjusting the rates of pumping the infusate, drained fluid and blood so as to remove a preselected amount of fluid from the blood.

7. The method of claim 6 further comprising monitoring the fluid pressure in the hemofiltration means to determine pressures and pressure differential and generating signals correlated thereto.

8. The method of claim 6 wherein said pumping of infusate to the hemofiltration means and said pumping of drained fluid from the hemofiltration means are controlled to occur only during said pumping of blood through the hemofiltration means.

9. Hemofiltation method for removal of fluid from the blood of a patient, comprising:

pumping blood from a patient through hemofiltration means and back to the patient;
   maintaining a supply of infusate in a first reservoir;
   pumping the infusate to the patient;
   monitoring the weight of the infusate and generating signals correlated thereto;
   pumping drained fluid from the hemofiltration means into a second reservoir;
   monitoring the weight of the drained fluid and generating signals correlated thereto;
   controlling the pumping of the blood, infusate and drained fluid by means of a computer programmed to operate the pumps for infusate and drained fluid only when the blood is being pumped, said computer being responsive to the infusate and drained fluid weight signals;
   said blood pumping operation being automatically responsive to signals generated by said computer to vary the flow rate of the blood through the hemofiltration means; and
   determining, at regular intervals, the weight of infusate in the firs reservoir and the weight of drained fluid in the second reservoir, comparing those weights to corresponding predetermined ideal weights and adjusting the rates of pumping the infusate, drained fluid and blood so as to remove a preselected amount of fluid from the blood.

10. The method of claim 9 further comprising monitoring the fluid pressure in the hemofiltration means to determine pressures and pressure differential and generating signals correlated thereto.

11. The method of claim 9 wherein said pumping of infusate to the patient and said pumping of drained fluid from the hemofiltration means are controlled to occur only during said pumping of blood through the hemofiltration means.

* * * * *

REEXAMINATION CERTIFICATE (3865th)

United States Patent [19]
Kitaevich et al.

[11] B1 5,344,568
[45] Certificate Issued *Sep. 7, 1999

[54] HEMOFILTRATION SYSTEM AND METHOD

[75] Inventors: Yuli Kitaevich, Milford; Nat Hemasilpin, Fairfield; J. Gabriel Marchevsky, Cincinnati; John J. Bissler, Cincinnati; George Benzing, III, Cincinnati; Paul T. McEnery, Cincinnati, all of Ohio

[73] Assignee: Children's Hospital Medical Center, Cincinnati, Ohio

Reexamination Request:
No. 90/004,927, Feb. 25, 1998

Reexamination Certificate for:
Patent No.: 5,344,568
Issued: Sep. 6, 1994
Appl. No.: 08/062,928
Filed: May 17, 1993

[ * ] Notice: This patent is subject to a terminal disclaimer.

Related U.S. Application Data

[63] Continuation of application No. 07/775,183, Oct. 11, 1991, Pat. No. 5,211,849.

[51] Int. Cl.[6] .............................. A61M 1/34; B01D 61/00; B01D 61/18; B01D 61/22
[52] U.S. Cl. .............................. 210/645; 210/85; 210/90; 210/96.1; 210/97; 210/134; 210/138; 210/143; 210/195.2; 210/257.1; 210/258; 210/321.71; 210/416.1; 210/433.1; 210/646; 210/739; 210/805; 210/929; 604/4; 604/5; 604/6
[58] Field of Search .............................. 210/85, 90, 96.1, 210/97, 101, 134, 138, 143, 195.2, 257.1, 257.2, 258, 259, 321.71, 416.1, 433.1, 645, 646, 649, 739, 805, 929; 604/4, 5, 6; 422/48; 177/45, 50

[56] References Cited

U.S. PATENT DOCUMENTS

| | | | |
|---|---|---|---|
| 4,132,644 | 1/1979 | Kolberg | 210/85 |
| 4,178,240 | 12/1979 | Pinkerton | 417/404 |
| 4,204,957 | 5/1980 | Weickhardt | 210/98 |
| 4,324,663 | 4/1982 | Hirel et al. | 210/646 |
| 4,372,846 | 2/1983 | Yamagami et al. | 210/929 |
| 4,582,598 | 4/1986 | Bilstad et al. | 210/101 |
| 4,606,826 | 8/1986 | Sano et al. | 210/929 |
| 4,684,460 | 8/1987 | Issautier | 210/90 |
| 4,728,433 | 3/1988 | Buck et al. | 210/646 |
| 4,767,399 | 8/1988 | Bollish | 604/5 |
| 4,769,132 | 9/1988 | Patono | 210/86 |
| 4,844,810 | 7/1989 | Richalley et al. | 210/646 |
| 4,889,635 | 12/1989 | Chevallet | 210/321.71 |
| 4,923,598 | 5/1990 | Schäl | 210/87 |
| 4,980,054 | 12/1990 | Lavender | 210/90 |
| 5,200,090 | 4/1993 | Ford et al. | 210/739 |
| 5,211,849 | 5/1993 | Kitaevich et al. | 210/645 |

FOREIGN PATENT DOCUMENTS

| | | |
|---|---|---|
| 0373455 | 9/1993 | European Pat. Off. . |
| 2397197 | 2/1979 | France . |

OTHER PUBLICATIONS

Hospal Instruction Manual BSM 22SC, Rev. A, pp. 29, 30 & 57, Mar. 1990.
COBE Centry System 3 Dialysis Control Unit Operator's Manual, pp. 1–21, 1–22, 3–29, 5–1, 5–2 & 7–9, Sep. 1988.
Sartorius Hemofilter (date unknown).

(List continued on next page.)

*Primary Examiner*—Sun Uk Kim

[57] ABSTRACT

A multipurpose hemofiltration system and method are disclosed for the removal of fluid and/or soluble waste from the blood of a patient. The system and method are equally applicable to adult, pediatric and neonatal patients. The system continuously monitors the weight of infusate in a first reservoir and drained fluid in a second reservoir and compares those weights to corresponding predetermined computed weights. When necessary, the pumping rates of the infusate, drained fluid and blood are adjusted in order to achieve a preselected amount of fluid removal from the patient's blood in a preselected time period. Application of this system and method provide repeatable and highly precise results.

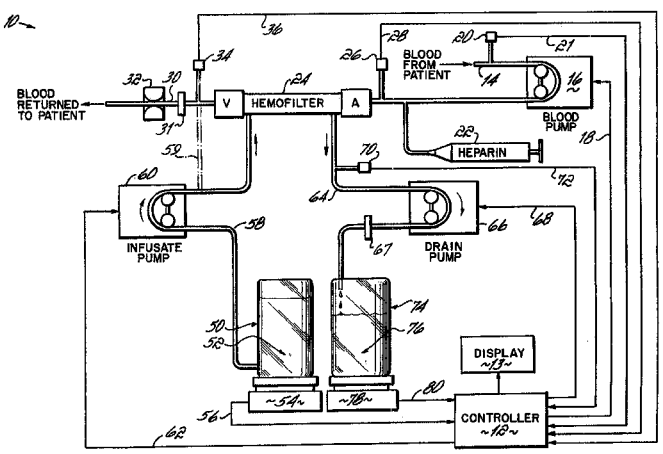

OTHER PUBLICATIONS

Sartorius Membranefilter Hemofilter and Hemoprocessor, A New System for Hemofiltration (date unknown).

Sartorius GmbH, Gottengen Germany, *Sartorius Hemoprocessor® 40020 Operating Instructions,* Sep. 1984.

Gambro AB, Lund, Sweden, *AK–10 System Operator's manual for hemofiltration BMM 10–1 and HFM 10–1,* May 1986.

J. H. Holmes et al., *Removal of Fluid From The Patient During Hemodialysis,* Dept. of Medicine, University of Colorado, Denver, Colorado, Mar., 1969.

E. P. Paganini, *Acute Continuous Renal Replacement Therapy,* Martinus Nijhoff Publishing, Boston, Massachusetts, 1986, pp. 91–111.

L. W. Henderson et al., *Hemofiltration,* Springer–Verlag, New York, 1986, pp. 83–89.

*International Standards for Medical Electrical Equipment, Part 2—Particular requirements for safety of hemodialysis equipment,* International Electrotechnical Commission, Geneva, Switzerland, 1989, pp. 1–57.

*Intensiv–behandlung, Zeitschrift fur Diagnostik, Therapie und Pflege,* International Conference on Continuous Hemofiltration, Baden, Austria, Sep. 1990, p. 110.

*Cobe CentrySystem 3 Precise Ultrafiltration Control,* Cobe Laboratories, Inc., Lakewood, Colorado, 1987.

*Hemofiltration in Perspective,* Gambro AB, Lund, Switerzerland, Oct. 1989.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

\* \* \* \* \*